US011452836B2

(12) United States Patent
Chang et al.

(10) Patent No.: US 11,452,836 B2
(45) Date of Patent: *Sep. 27, 2022

(54) SYSTEM AND METHOD FOR PREVENTING CROSS-CONTAMINATION IN FLOW GENERATION SYSTEMS

(71) Applicant: Invent Medical Corporation, Carlsbad, CA (US)

(72) Inventors: Samuel M. Chang, Poway, CA (US); Nhien M. Nguyen, Santa Ana, CA (US)

(73) Assignee: INVENT MEDICAL CORPORATION, Carlsbad, CA (US)

( * ) Notice: Subject to any disclaimer, the term of this patent is extended or adjusted under 35 U.S.C. 154(b) by 185 days.

This patent is subject to a terminal disclaimer.

(21) Appl. No.: 16/735,463

(22) Filed: Jan. 6, 2020

(65) Prior Publication Data
US 2020/0139067 A1    May 7, 2020

Related U.S. Application Data

(63) Continuation of application No. 15/405,512, filed on Jan. 13, 2017, now Pat. No. 10,525,222.
(Continued)

(51) Int. Cl.
*A61M 16/10* (2006.01)
*A61M 16/00* (2006.01)
(Continued)

(52) U.S. Cl.
CPC .... *A61M 16/1065* (2014.02); *A61M 16/0069* (2014.02); *A61M 16/022* (2017.08);
(Continued)

(58) Field of Classification Search
CPC ............ A61M 16/0069; A61M 16/205; A61M 16/022; A61M 16/0883; A61M 16/1055;
(Continued)

(56) References Cited

U.S. PATENT DOCUMENTS 3,815,754 A    6/1974    Rosenberg
4,653,493 A    3/1987    Hoppaugh
(Continued)

FOREIGN PATENT DOCUMENTS

EP    0533644 A2    3/1993
JP    3691473 B2    9/2005
(Continued)

*Primary Examiner* — James D Ponton
(74) *Attorney, Agent, or Firm* — Procopio, Cory, Hargreaves & Savitch LLP (57) ABSTRACT

A system for preventing cross-contamination in single-limb ventilators is described. In one embodiment, the system includes an airflow generator connected in-line to a humidifier, a first check valve and a patient interface by a gas flow circuit. A controller is electrically coupled to the airflow generator, and a cartridge is connected to the gas flow circuit between a first point downstream of the humidifier and a second point upstream of the patient interface. The cartridge includes a bacteria filter and the first check valve. A method for preventing cross-contamination in single-limb ventilators and a method for providing gaseous flow through a single-limb ventilator are also described.

19 Claims, 11 Drawing Sheets

Related U.S. Application Data (60) Provisional application No. 62/288,058, filed on Jan. 28, 2016.

(51) Int. Cl.
| | | |
|---|---|---|
| *A61M 16/08* | (2006.01) | |
| *A61M 16/20* | (2006.01) | |
| *A61M 16/16* | (2006.01) | |
| *A61M 16/12* | (2006.01) | |

(52) U.S. Cl.
CPC .... *A61M 16/0883* (2014.02); *A61M 16/1055* (2013.01); *A61M 16/16* (2013.01); *A61M 16/205* (2014.02); *A61M 16/208* (2013.01); *A61M 16/0875* (2013.01); *A61M 16/125* (2014.02); *A61M 2016/003* (2013.01); *A61M 2016/0027* (2013.01); *A61M 2016/0036* (2013.01); *A61M 2016/0039* (2013.01); *A61M 2205/123* (2013.01); *A61M 2205/128* (2013.01)

(58) Field of Classification Search
CPC .......... A61M 16/1065; A61M 16/0875; A61M 16/16; A61M 16/20; A61M 16/208; A61M 2016/003; A61M 2205/12; A61M 2205/128
See application file for complete search history.

(56) References Cited

U.S. PATENT DOCUMENTS

| | | | |
|---|---|---|---|
| 4,727,871 | A | 3/1988 | Smargiassi |
| 5,237,987 | A | 8/1993 | Anderson et al. |
| 5,349,946 | A | 9/1994 | McComb |
| 5,660,171 | A | 8/1997 | Kimm et al. |
| 5,823,186 | A | 10/1998 | Rossen et al. |
| 6,131,571 | A | 10/2000 | Lampotang et al. |
| 6,279,574 | B1 | 8/2001 | Richardson et al. |
| 6,668,824 | B1 | 12/2003 | Isaza et al. |
| 7,497,215 | B1* | 3/2009 | Nguyen ............ A61M 16/0057 128/204.17 |
| 8,047,205 | B2 | 11/2011 | Von Blumenthal et al. |
| 2007/0044799 | A1 | 3/2007 | Hete et al. |
| 2007/0144516 | A1* | 6/2007 | Doyle ............... A61M 16/0883 128/204.18 |
| 2008/0027372 | A1 | 1/2008 | Baldwin |
| 2009/0071479 | A1 | 3/2009 | Nguyen et al. |
| 2009/0247967 | A1 | 10/2009 | Paoli |
| 2010/0175695 | A1* | 7/2010 | Jamison ................ A61M 16/12 128/203.14 |
| 2012/0006326 | A1 | 1/2012 | Ahmad |
| 2013/0220325 | A1* | 8/2013 | Davis ................ A61M 16/0057 128/204.23 |
| 2013/0253336 | A1 | 9/2013 | Haver |
| 2014/0230815 | A1 | 8/2014 | Gribb et al. |

FOREIGN PATENT DOCUMENTS

| | | |
|---|---|---|
| JP | 2014530537 | 11/2014 |
| WO | 2015174861 A1 | 11/2015 |

\* cited by examiner

SYSTEM AND METHOD FOR PREVENTING CROSS-CONTAMINATION IN FLOW GENERATION SYSTEMS

CROSS-REFERENCE TO RELATED APPLICATIONS

This application is a continuation of U.S. patent application Ser. No. 15/405,512, filed Jan. 13, 2017, which claims priority to U.S. Provisional Application No. 62/288,058, filed on Jan. 28, 2016, both of which are incorporated herein by reference in their entireties.

BACKGROUND OF THE INVENTION

Flow generation systems can be generally described as systems that generate a gaseous flow, for example airflow or a blend of ambient air and oxygen. A ventilator is one example of a flow generation system. A ventilator is a piece of medical equipment that delivers a flow of gas, such as a blend of oxygen and ambient air to the airway of a patient to assist in or substitute a patient's breathing. Most ventilators deliver a blend of oxygen and air so that the patient receives a target oxygen concentration greater than that of ambient air. Generally, ventilators utilize a combination of single-use or reusable disposable components for the patient interface (e.g. a mask or mouthpiece connected to flexible tubing) and non-disposable capital equipment (e.g. air pumps, sensors, controller modules, humidifiers, etc.) that is used over a period of time among different patients. The patient interface can be for example a mouthpiece, mask (full face, nasal, pillow, total mask, or combinations of these), endotracheal tube or tracheostomy tube.

Although there are a variety of ventilator designs currently used in the field, most conventional designs will fall into either the single-limb or double-limb category. Single-limb ventilators typically come in different configurations. In certain types of single limb configurations, there is no "active" exhalation valve. Instead, a hole (or multiple holes) at or near the patient connection serves as a "passive" exhalation valve. However, in this configuration, since the hole(s) is not big enough to handle the entire exhalation flow, some of the exhaled flow travels back to the device. In an acute care single-limb circuit, a single tube is also used for inhalation and exhalation. Typically, a section of the tube near the patient's mouthpiece is equipped with an exhalation valve, which is switched on and off according to a pressure and/or flow signal measured by the system. The pressure and/or flow signal can detect when air is flowing from the ventilator equipment to the patient, causing the exhalation valve to stay closed. The pressure and/or flow signal can also detect when air stops flowing, or when an upstream airflow is detected, causing the exhalation valve to open. Double limb circuits are similar, except that they have a second tube connecting back to the ventilator, where the exhalation valve is located in this case. The advantage of a single limb circuit is that it eliminates the issues of added bulk, weight and production costs that are present with double limb design. However, one of the shortcomings of single-limb ventilators is cross-contamination of the ventilator, since exhaled gas from the patient can return to the dedicated or non-disposable components of the ventilator system during exhalation.

Figure 1:
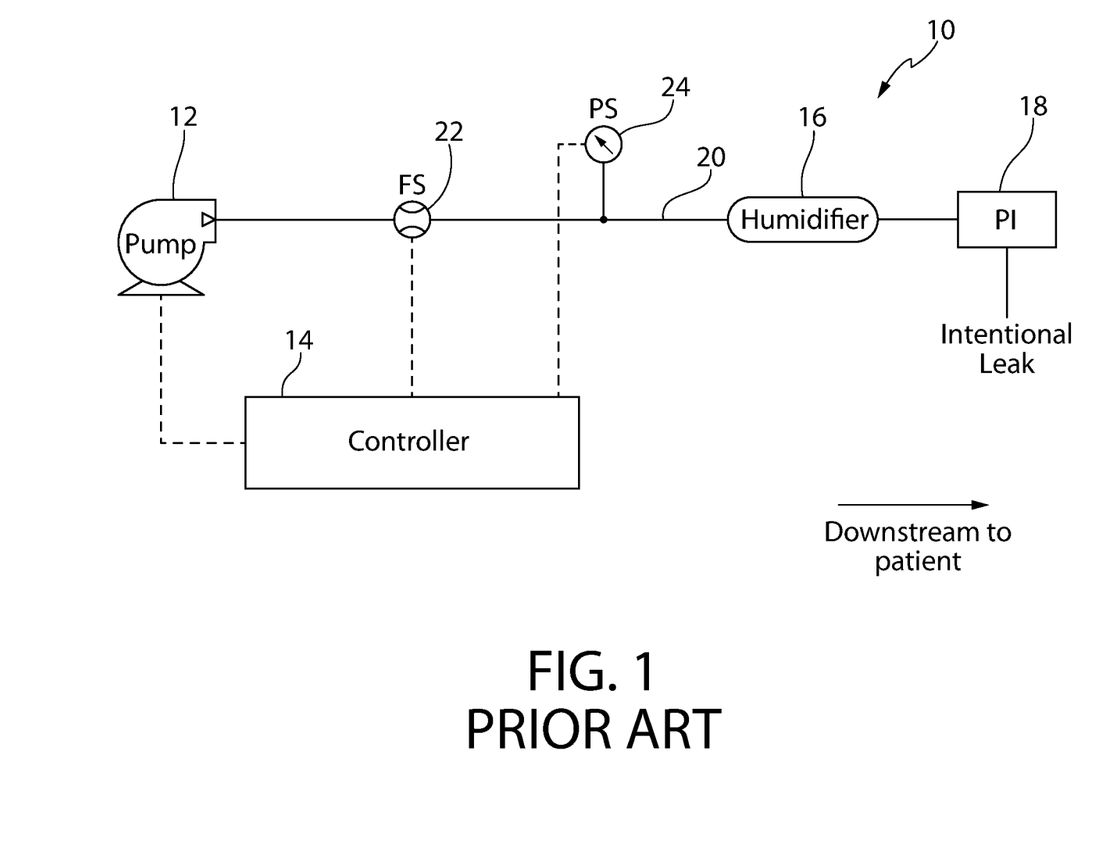
FIG. 1 is a pneumatic schematic circuit of a prior art ventilator system.

With reference now to prior art FIG. 1, a conventional single limb ventilator circuit 10 is shown in the pneumatic schematic circuit diagram. An air pump 12 is connected via an in-line gas flow circuit 20 to a humidifier 16 and a patient interface 18. The patient interface 18 can include the single-limb flexible patient tubing and a patient interface for the patient to breathe through. A flow sensor 22 and a pressure sensor 24 are positioned in the gas flow circuit 20, and they communicate measurements to a controller 14 that controls the air pump 12. As demonstrated by the diagram, the equipment in this blower based single-limb ventilator is exposed to contamination from the patient's exhaled gas.

Figure 2A:
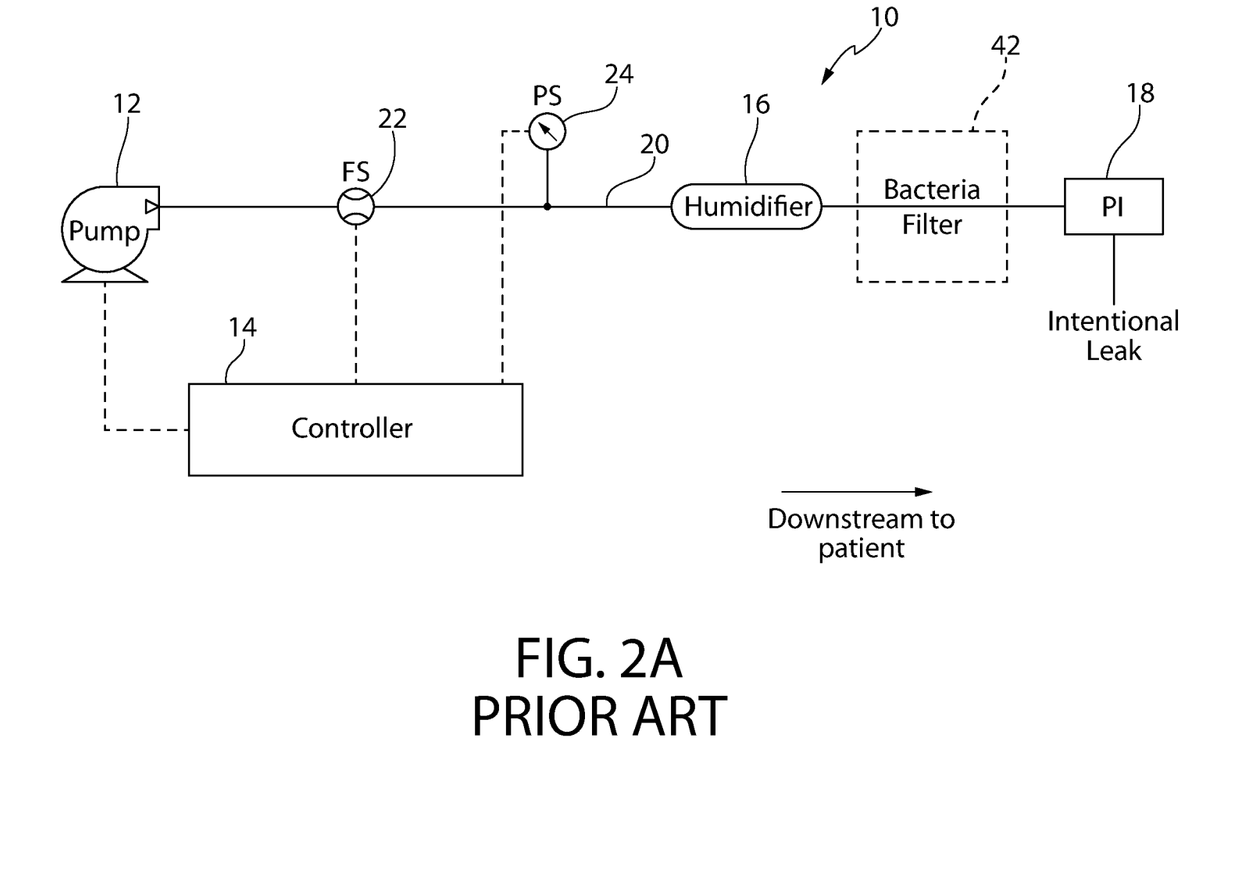
FIG. 2A is a pneumatic schematic circuit of a prior art ventilator system having an integrated humidifier.
Figure 2B:
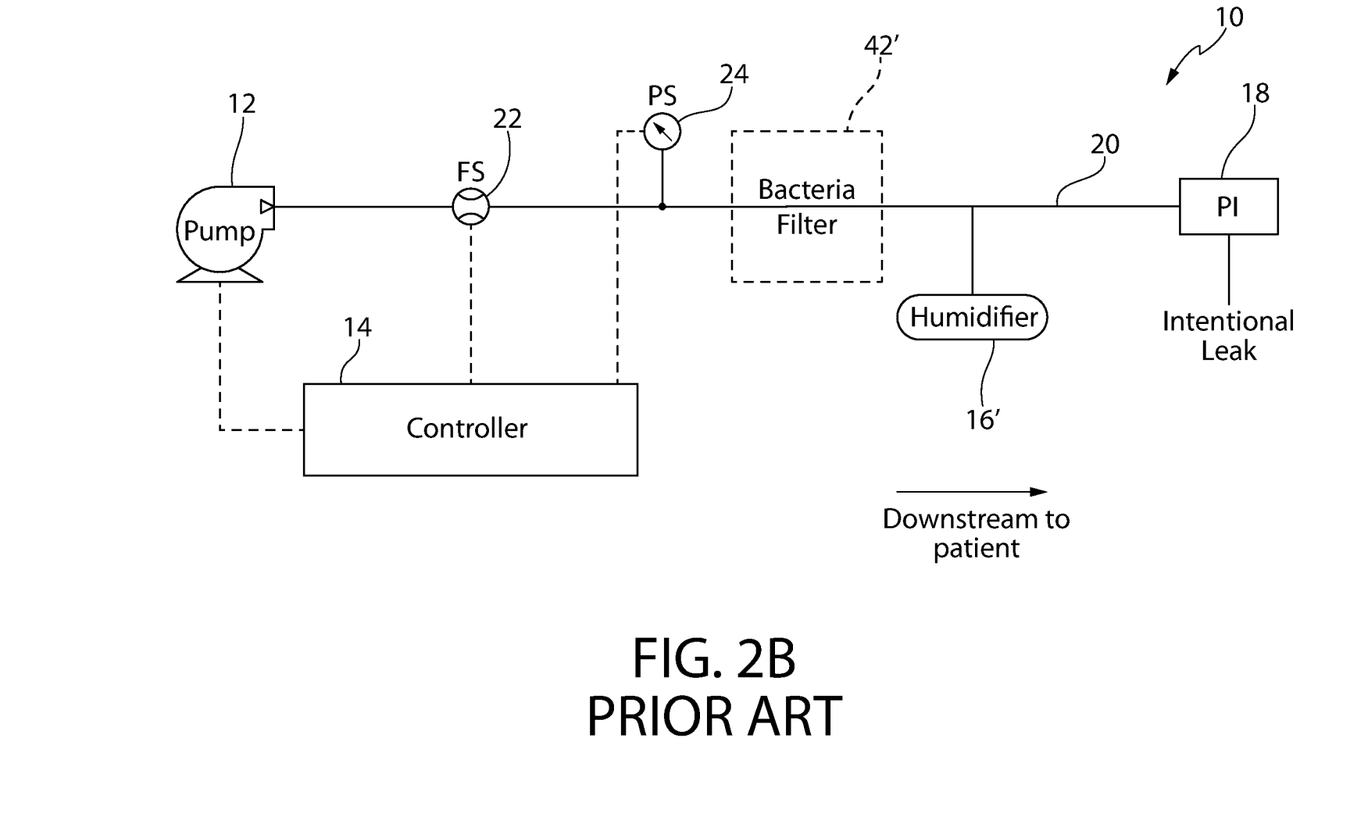
FIG. 2B is a pneumatic schematic circuit of a prior art ventilator system having an external humidifier.

Currently, the only recommended method in preventing cross-contamination is to add bacteria filters 42 at the ventilator outlet, as shown for example in prior art FIG. 2A. If the medical facility or patient fails to use bacteria filters, the main body of the ventilator components are exposed to the patient exhaled gas, and subsequently susceptible to contamination. In addition to the potential cross-contamination, for the cases of bacteria filter use, there are at least a couple of scenarios which could affect the proper ventilator functions. Many ventilator systems include integrated humidifiers, although some do not. Humidifiers (heated or non-heated) are usually required for patients who are on ventilators. Typically, for ventilator systems that include integrated humidifiers, the bacteria filter is located downstream of the humidifier (see for example FIG. 2A). However, one issue with locating a bacteria filter downstream of the integrated humidifier is that water vapor in the gas often leads to improper function of ventilator components, negatively affecting proper ventilator function. In the case of a ventilator system that is not equipped with an integrated humidifier, such as systems that use an external humidifier 16' (see for example FIG. 2B), the bacterial filter 42' can be located downstream or upstream of the external humidifier 16'. However, even for systems that utilize an external humidifier 16', where the bacteria filter 42' can be located between the ventilator outlet and the humidifier inlet, the chances of the bacteria filter 42' being compromised due to the humidified gas will remain high, again affecting proper operation of the components of the ventilators. Some ventilators (or mainly sleep apnea therapy devices) are designed to be used without bacteria filters altogether (see for example FIG. 1). In this case, ventilators and their components are naturally susceptible to contamination.

Thus, what is needed in the art is a ventilator system that can more effectively utilize a bacterial filter and a humidifier while minimizing the risk of cross-contamination to dedicated ventilator components and devices.

SUMMARY OF THE INVENTION

In one embodiment, a system for preventing cross-contamination in a flow generation apparatus includes an airflow generator connected in-line to a humidifier, a first check valve and a patient interface connection by a first gas flow circuit; a controller electrically coupled to the airflow generator; and a second check valve connected in-line to a bacterial filter along a second gas flow circuit, the second gas flow circuit connected to the first gas flow circuit between a first junction upstream of the humidifier and a second junction downstream of the first check valve; where a removable cartridge houses the bacterial filter and the first check valve. In one embodiment, the removable cartridge houses the second junction. In one embodiment, an exhalation valve is electrically coupled to the controller and connected to the gas flow circuit downstream of the airflow generator and upstream of the humidifier. In one embodiment, a housing includes a cavity configured for accepting insertion of the cartridge. In one embodiment, the insertion includes slidable, screw or quick connect insertion. In one embodiment, the cavity is configured for allowing removal of the cartridge. In one embodiment, the removal includes slidable, screw or quick disconnect removal. In one embodiment, the housing at least partially defines at least one of the first and second gas flow circuit. In one embodiment, the housing includes a locking mechanism for securing the cartridge within the cavity. In one embodiment, openings of the first and second gas flow circuit are configured to interface with openings of the cartridge upon insertion. In one embodiment, the first check valve is configured to restrict the upstream flow of gas. In one embodiment, the second check valve is configured to restrict the downstream flow of gas. In one embodiment, a flow sensor is electrically coupled to the controller and connected to the gas flow circuit downstream of the pump and upstream of the humidifier. In one embodiment, a pressure sensor is electrically coupled to the controller and connected to the first gas flow circuit downstream of the pump and upstream of the humidifier. In one embodiment, the airflow generator is one of a blower and a pressure generator. In one embodiment, the exhalation valve is one of a voice coil actuator, stepper motor valve, proportional solenoid valve and pneumatically piloted balloon valve. In one embodiment, the cartridge includes an autoclavable medical grade material. In one embodiment, at least one of the first and second gas flow circuit includes a flexible plastic tubing. In one embodiment, at least one of the first and second gas flow circuit includes rigid or manifold tubing.

In one embodiment, a method for providing gaseous flow through a flow generation apparatus includes the steps of providing a downstream gaseous flow to a first junction, where the first junction has a first branch including an inhalation circuit and a second branch including an exhalation circuit, where the inhalation circuit includes a humidifier in line with a first check valve, where the exhalation circuit includes a second check valve in-line with a bacterial filter, and where the inhalation circuit and the exhalation circuit extend to and merge downstream of the first junction at a second junction; preventing gas from traveling through at least a portion of the exhalation circuit during an inhalation phase; and preventing unfiltered gas from traveling through at least a portion of the exhalation circuit during an exhalation phase. In one embodiment, a portion of the exhalation circuit including the bacteria filter and the inhalation circuit including the first check valve is housed in a removable cartridge. In one embodiment, the second junction is housed in the removable cartridge. In one embodiment, the second junction is connected to a patient interface connection. In one embodiment, the method includes the step of exhausting an upstream gaseous flow of air at a point upstream of the first junction during the exhalation phase. In one embodiment, at least one of the first and second check valves is a pressure actuated check valve. In one embodiment, the exhalation phase is detected by one of a flow sensor and a pressure sensor upstream of the first junction. In one embodiment, the gaseous flow includes a blend of oxygen and ambient air.

In one embodiment, a method for preventing cross-contamination in a flow generation apparatus includes removing a used cartridge from a cavity in a flow generation apparatus, the cartridge including a bacterial filter and a first check valve, the system including an airflow generator connected in-line to a humidifier, the first check valve and a patient interface connection by a first gas flow circuit, a second gas flow circuit connected to the first gas flow circuit between a first junction upstream of the humidifier and a second junction downstream of the first check valve, and a housing including the cavity, the housing configured so that the first check valve is connected in-line with the first gas flow circuit when the cartridge is fully inserted into the cavity, and the bacterial filter is connected in-line with a second gas flow circuit when the cartridge is fully inserted into the cavity; and inserting a prepared cartridge into the cavity. In one embodiment, the method includes the step of autoclaving a used cartridge to the prepared cartridge before the step of inserting. In one embodiment, the method includes disposing the used cartridge and providing a prepared cartridge. In one embodiment, the method includes the step of performing a first treatment on a first patient prior to the step of removing the used cartridge, where the first treatment utilizes the system for assisting the first patient's breathing. In one embodiment, the method includes the step of performing a second treatment on a second patient after the step of autoclaving the cartridge, where the second treatment utilizes the system for assisting the second patient's breathing. In one embodiment, the method includes the step of measuring at least one of a flow and a pressure within the gas flow circuit downstream of the airflow generator and upstream of the humidifier; and opening an exhalation valve based on the measuring. In one embodiment, the method includes the step of restricting upstream movement of gas at a point between the patient interface connection and the humidifier. In one embodiment, the method includes the step of restricting downstream movement of gas at a point between the bacterial filter and the patient interface connection. In one embodiment, the method includes the step of slidably removing the used cartridge. In one embodiment, the method includes the step of slidably inserting the autoclaved cartridge. In one embodiment, the method includes the step of locking the cartridge within the cavity. In one embodiment, the method includes the step of interfacing openings of the gas flow circuit with openings of the cartridge upon insertion.

In one embodiment, a system for preventing cross-contamination in a flow generation apparatus includes an airflow generator connected in-line to a humidifier, a first check valve and a patient interface connection by a gas flow circuit; a controller electrically coupled to the airflow generator; and a cartridge receiving cavity connected to the gas flow circuit between a first point downstream of the humidifier and a second point upstream of the humidifier. In one embodiment, an exhalation valve is electrically coupled to the controller and connected to the gas flow circuit downstream of the airflow generator and upstream of the humidifier. In one embodiment, the cartridge receiving cavity is configured for slidable, screw or quick connect insertion of a cartridge. In one embodiment, the cartridge receiving cavity is configured for allowing removal of a cartridge. In one embodiment, the housing at least partially defines the gas flow circuit. In one embodiment, housing includes a locking mechanism for securing a cartridge within the cavity. In one embodiment, openings of the gas flow circuit are configured to interface with openings of a cartridge upon insertion. In one embodiment, the first check valve is configured to restrict the upstream flow of gas. In one embodiment, a second check valve is configured to restrict the downstream flow of gas. In one embodiment, a flow sensor is electrically coupled to the controller and connected to the gas flow circuit downstream of the pump and upstream of the humidifier. In one embodiment, a pressure sensor is electrically coupled to the controller and connected to the gas flow circuit downstream of the pump and upstream of the humidifier. In one embodiment, the airflow generator is one of a blower and a pressure generator. In one embodiment, the exhalation valve is one of a voice coil actuator, stepper motor valve, proportional solenoid valve and pneumatically piloted balloon valve. In one embodiment, the gas flow circuit includes a flexible plastic tubing. In one embodiment, the gas flow circuit includes rigid or manifold tubing.

In one embodiment, a cartridge for a flow generation apparatus includes an inhalation circuit including a first check valve; and an exhalation circuit including a bacterial filter; where the inhalation circuit and the exhalation circuit merge at a junction downstream of the first check valve and the bacterial filter. In one embodiment, the inhalation circuit is connected to a first opening in a housing of the cartridge. In one embodiment, the exhalation circuit is connected to a second opening in a housing of the cartridge. In one embodiment, the junction is connected to a third opening in a housing of the cartridge.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

It is to be understood that the figures and descriptions of the present invention have been simplified to illustrate elements that are relevant for a more clear comprehension of the present invention, while eliminating, for the purpose of clarity, many other elements found in systems and methods of preventing cross-contamination in single-limb ventilators. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is are systems and methods for preventing cross-contamination in single-limb ventilators.

Figure 3:
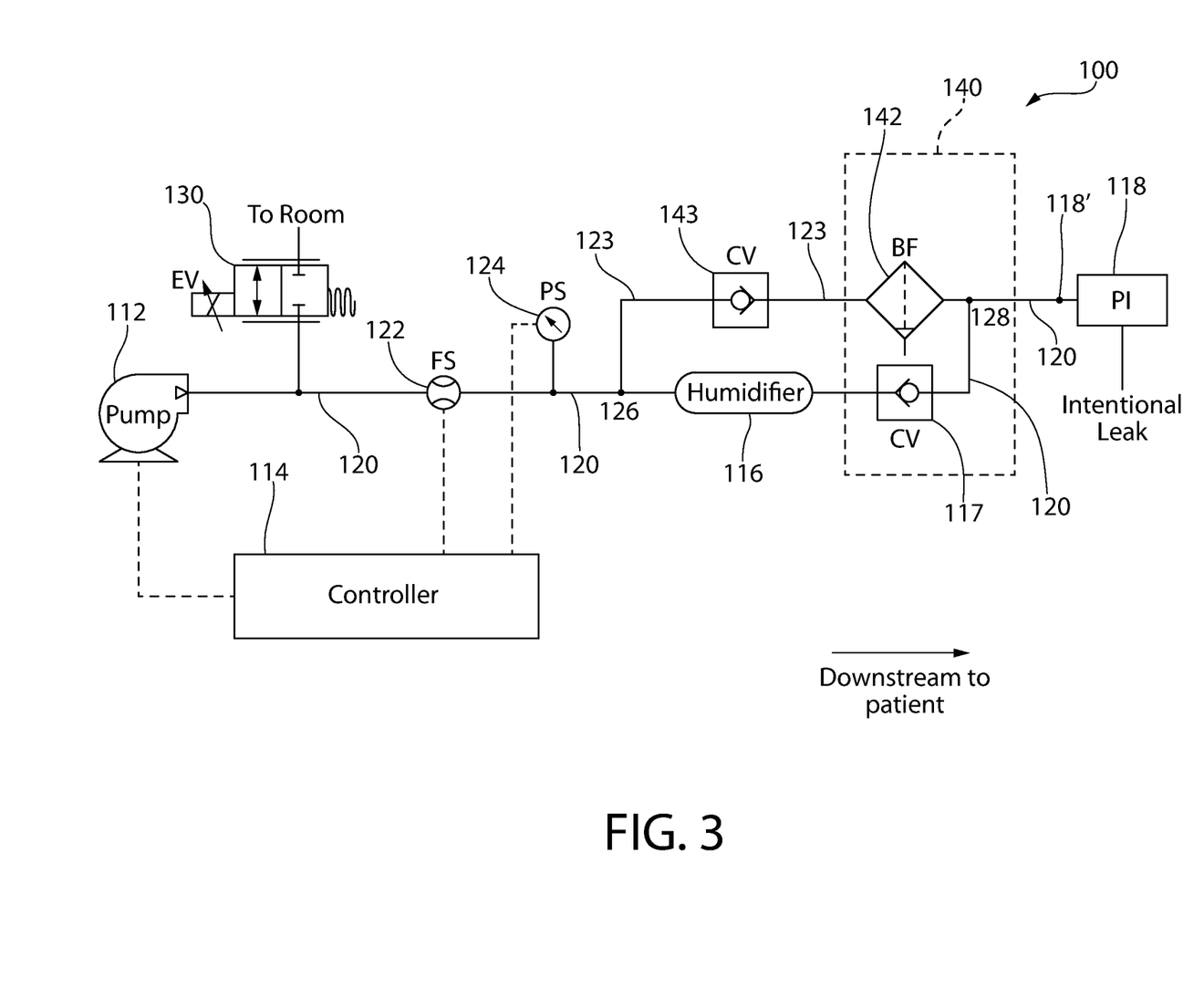
FIG. 3 is a pneumatic schematic circuit of a ventilator system according to one embodiment.

As shown in the system pneumatic schematic circuit of FIG. 3, the system 100 according to one embodiment includes an airflow generator 112 connected in-line to a humidifier 116, a first check valve 117 and a patient interface 118. These components are connected by a first gas flow circuit 120, which in certain embodiments, can be formed by openings or rigid tubular structures defined by the system housing(s), connections by flexible tubing, or a combination of both. In one embodiment, the gas flow circuit includes rigid or manifold tubing. In certain embodiments, the humidifier is replaced by an empty chamber or a void. The airflow generator 112 can be of types known in the art, such as blowers, fans, or pressure generators. In certain embodiments, the check valve is a resilient one-way valve, such as a duckbill valve. The check valve can also be a 2-way valve this is electronically controlled by the controller 114 or a pneumatically piloted 2-way valve. The first check valve 117 is configured to restrict the upstream flow of gas. The second check valve 143 is configured to restrict the downstream flow of gas. A controller 114 is wired to the pump, and it sends drive signals to the pump during operation. The controller 114 can store program or historical data for controlling the breathing patterns of the patient. The controller 114 can also relay calculate drive signals for the air pump and valves within the system, based on programed software and/or feedback from sensors in the system. A cartridge 140 houses part of the first gas flow circuit 120, the first check valve 117 and the bacterial filter 142. The cartridge 140 also houses part of the second gas flow circuit 123. A second gas flow circuit 123 connects a second check valve in-line with the bacterial filter. The cartridge 140 is installed downstream of a first junction 126 located upstream of the humidifier 116, and the cartridge 140 includes a second junction 128 located downstream of the humidifier 116, the cartridge further including the first check valve 117. The branch of the second gas flow circuit 123 including the second check valve 143 and the bacterial filter 142, extending between the first junction 126 and the second junction 128 may be referred to as the exhalation circuit in certain embodiments. The branch of the first gas flow circuit including the humidifier 116 and the first check valve between the first junction 126 and the second junction 128 may be referred to as the inhalation circuit in certain embodiments.

Figure 4A:
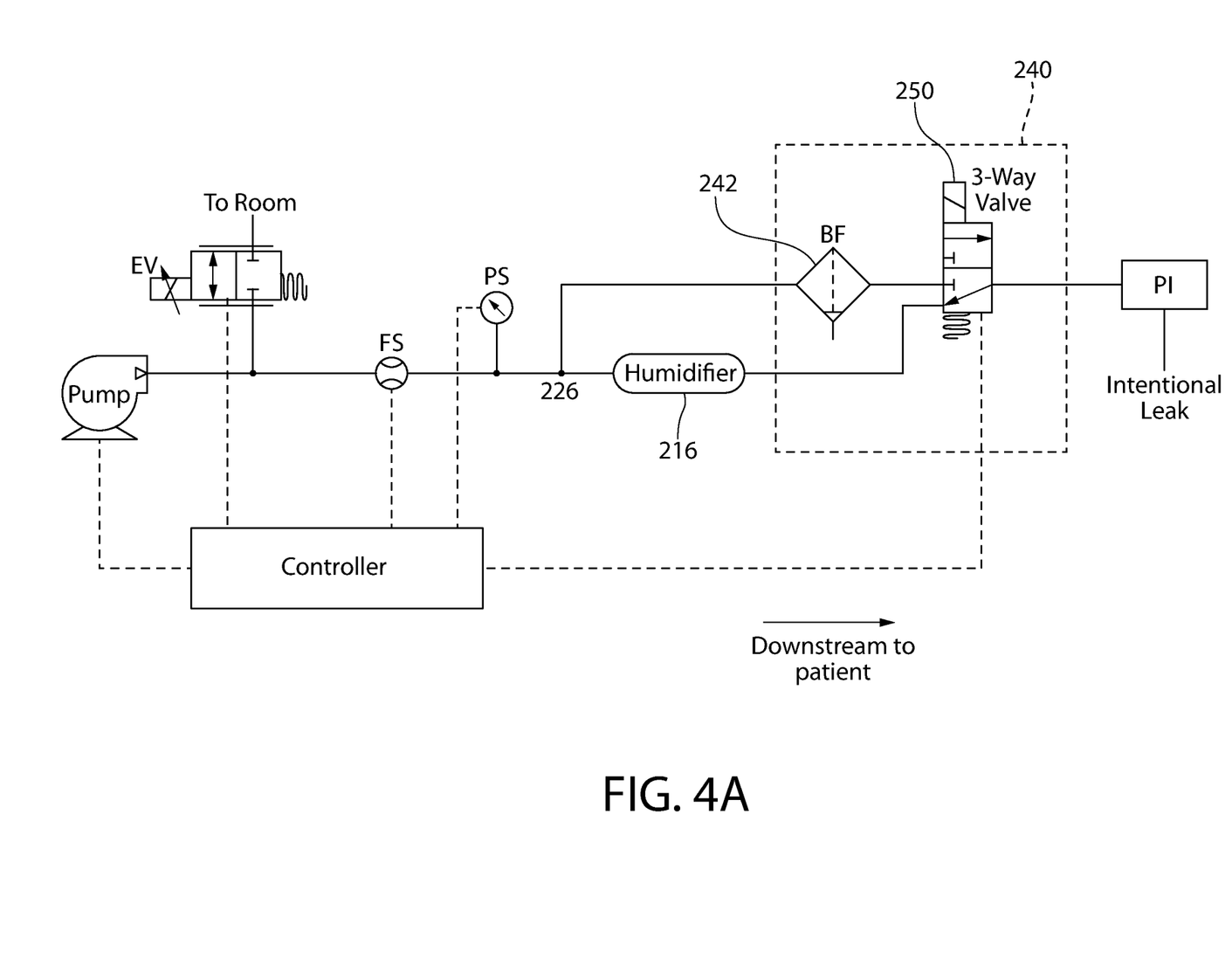
FIG. 4A is a pneumatic schematic circuit of a ventilator system with a 3-way valve directing exhaled flow to a junction according to one embodiment.
Figure 4B:
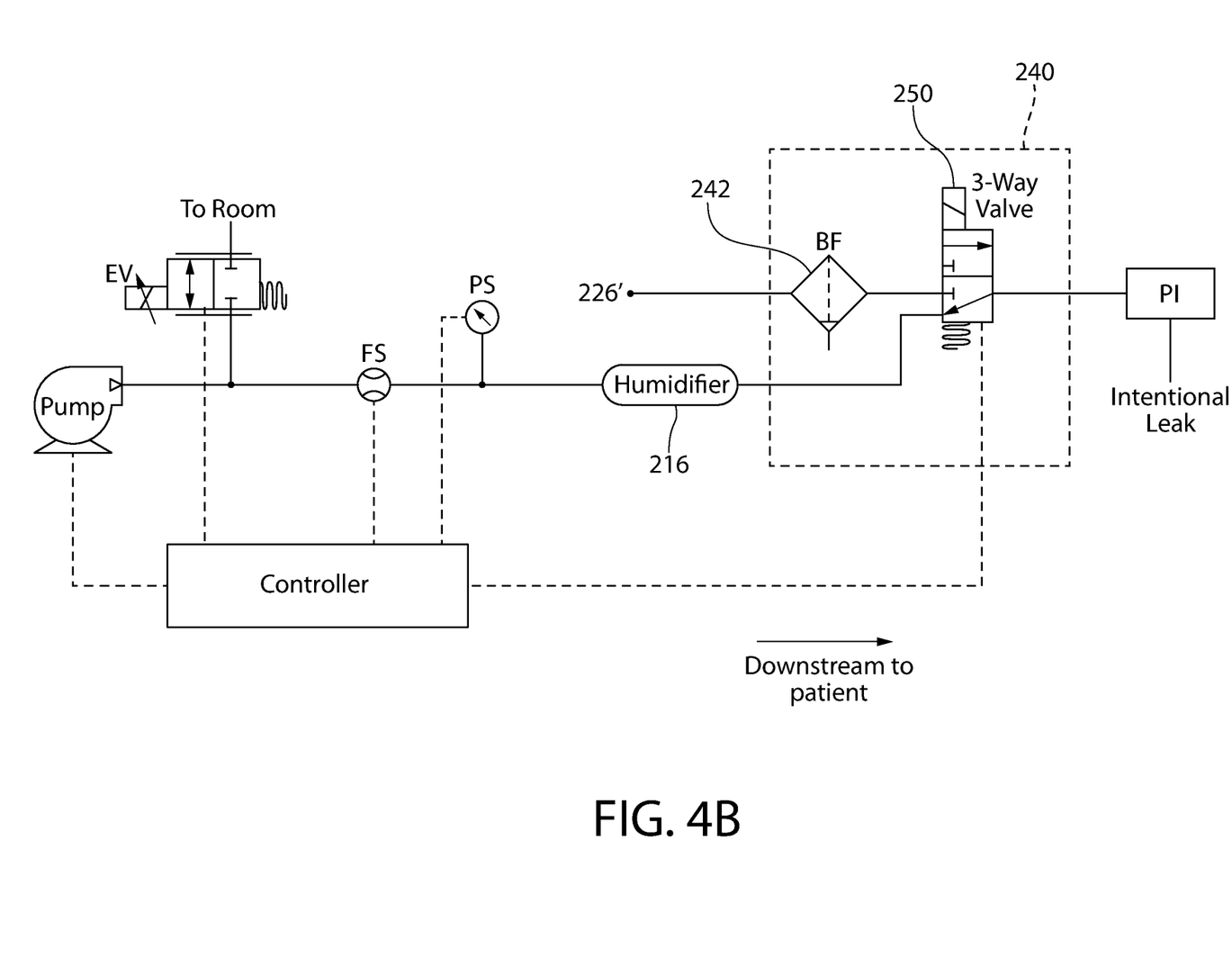
FIG. 4B is a pneumatic schematic circuit of a ventilator system with a 3-way valve directing exhaled flow to a room air port according to one embodiment.

Junctions 126 and 128 may be open junctions that allow the free flow of gas throughout the connected gas lines at the junctions. In certain embodiments, one or both of the junctions 126, 128 are 3-way valves that can be controlled electronically via the controller 114, pneumatically piloted or actuated by a pressure gradient during inspiration and exhalation. For example, with reference to FIG. 4A, in one embodiment, the cartridge 240 houses a 3-way valve 250 that directs flow from the humidifier 216, to the PI (or junction between the 3-way valve and the PI), or directs the exhaled flow to the first junction 226. In another embodiment, with reference now to FIG. 4B, instead of venting to junction 226 (shown in FIG. 4A), the 3-way valve instead vents to a room air port 226'. With reference back to FIG. 3, in certain embodiments, if a 3-way valve is used at a junction 126, 128, the redundant first and/or second check valves 117, 143 can be removed. If the second junction 128 uses a three way valve, it can optionally be housed within the cartridge 140. The second check valve 143 can optionally be included within the cartridge 140. In one embodiment, a junction valve is located at the second junction 128. In certain embodiments, the junction valve is configured to limit or block gas access to a particular branch of the junction when gas transfer to that branch is not desired. For example, in one embodiment, a junction valve located at the second junction 128 has a first position during an inhalation phase, blocking the downstream gas flow to the bacteria filter 142, and a second position during an exhalation phase, blocking downstream gas flow to the humidifier 116. Similarly, and in addition, a junction valve can be located at junction 128 that has a first position during an inhalation phase, blocking upstream gas flow to the bacteria filter, and a second position during exhalation, blocking upstream access to the humidifier. In this case, the junction valve can be housed within the cartridge. The junction valve can be a flexible pressure actuated check valve, or an actuating valve that communicates with the controller 114 for receiving control signals to open or close corresponding with inhalation and exhaustion. In certain embodiments, the patient interface 118 includes a connection port 118' and the flexible tubing, mask and/or mouthpiece that the patient breathes directly into. In certain embodiments, the patient interface includes masks (e.g. nasal, full, total, pillow, or combinations of these), a mouth piece, an endotracheal tube or a tracheostomy tube. According to certain embodiments, the patient interface 118 may or may not have intentional leakage. Intentional leakage at the patient interface in the figures is shown merely as an example embodiment. The cartridge 140 is a removable cartridge that includes a bacteria filter 142 connected-in line to the second check valve 143. The cartridge 140 in certain embodiments is constructed of materials such as medical grade plastics that are capable of withstanding high temperature sterilization, are autoclaveable, or are similar of withstanding some type of sterilization or autoclaving chamber. In certain embodiments, the cartridge 140 is constructed for single or limited use as a disposable component. As shown in the circuit of FIG. 3, the position of the cartridge 140 prevents cross-contamination between patients via the bacterial filter by preventing the return of unfiltered air that could be contaminated back to the main body of the ventilator components such as the airflow generator 112. In certain embodiments where a junction valve is used, patient exhaled gas is prevented from returning to the main body of the ventilator (e.g. junction 126 and upstream), and can optionally be vented out to atmosphere. The position of the cartridge 140 also makes it simple to be replaced between patients.

In one embodiment, the system 100 includes an exhalation valve 130 wired to the controller 114 and connected to the gas flow circuit 120 downstream of the airflow generator 112 and upstream of the humidifier 116. The exhalation valve 130 can in certain embodiments be one of a voice coil actuator, stepper motor valve, proportional solenoid valve or a pneumatically piloted balloon valve. The exhalation valve 130 receives a signal from the controller 114 to open or shut, and can also receive an instruction for partially opening. In certain embodiments, the exhalation valve 130 is located at the first junction 126, between the first junction 126 and the second check valve 143, or between the second check valve 143 and the bacterial filter 142. In certain embodiments, the first junction 126 is eliminated when the exhalation valve 130 is located along the exhalation circuit 123. A second exhalation valve or leak port for passive exhalation can be located at the first junction 126, between the first junction 126 and the second check valve 143, or between the second check valve 143 and the bacterial filter 142. Some or all of the bacterial filter 142, second check valve 143, exhalation valve 130 and an exhalation leak port can be implemented as a single component. One or more flow sensors 122 and pressure sensors 124 can be present within the gas flow circuit 120. In one embodiment, a flow sensor 122 is wired to the controller 114 and connected to the gas flow circuit 120 downstream of the pump 112 and upstream of the humidifier 116. A flow sensor can be placed along the exhalation circuit 123 for embodiments where the exhalation valve 130 is placed along the exhalation circuit (e.g. after the exhalation valve 130 when the exhalation valve 130 is between the second check valve 143 and the bacterial filter 142). In one embodiment, a pressure sensor 124 is wired to the controller 114 and connected to the gas flow circuit 120 downstream of the pump 112 and upstream of the humidifier 116. The flow and pressure sensors can receive measurements that indicate and measure events such as pump airflow, exhalation airflow, pump pressure, exhalation pressure, etc. The controller 114 can use these measurements to control airflow and exhalation levels accordingly, based on the desired treatment begin administered to the patient.

Figure 5:
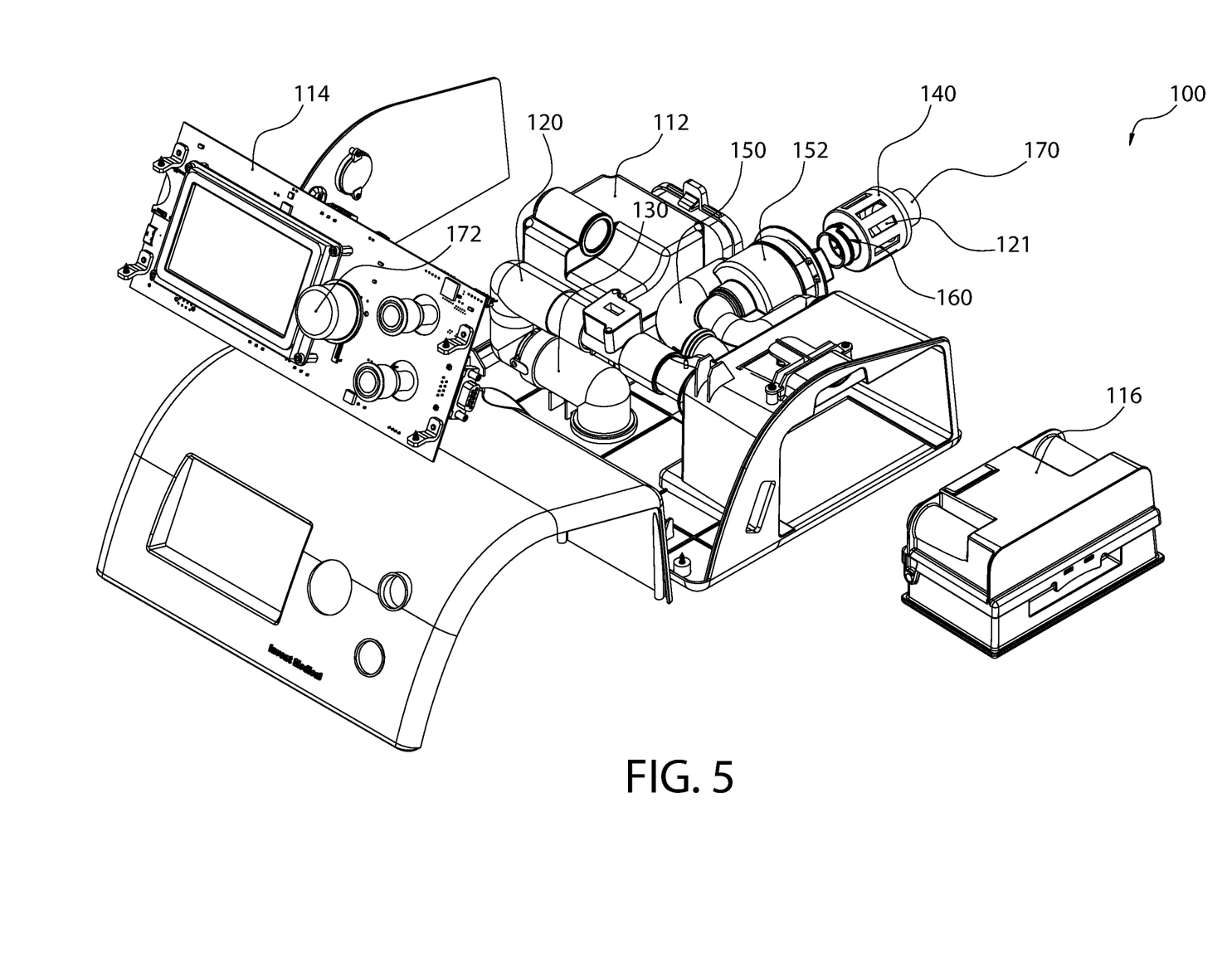
FIG. 5 is an exploded view of a ventilator system according to one embodiment.
Figure 6A:
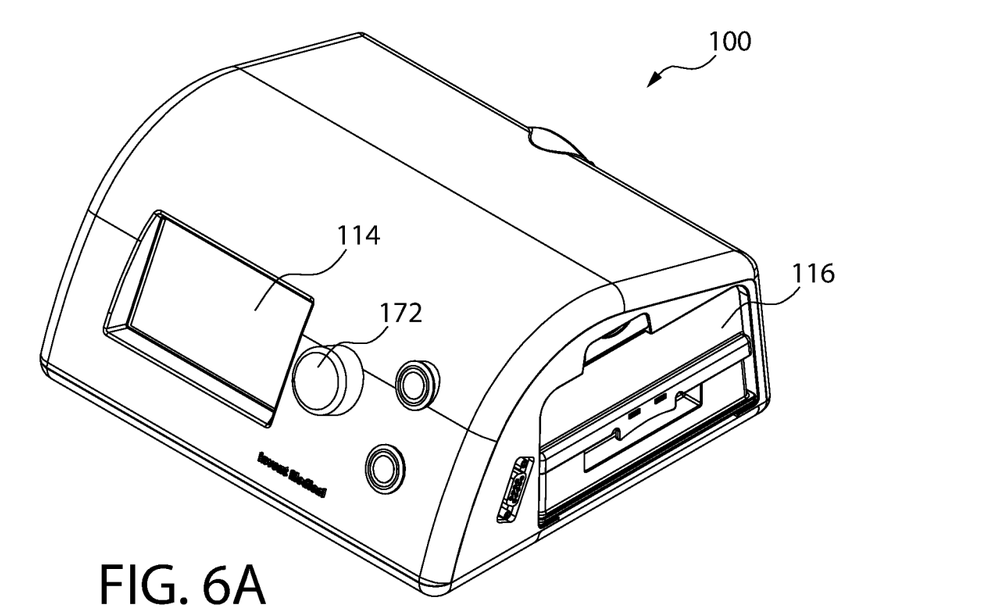
FIG. 6A is a perspective view of assembled components of a ventilator system and the cartridge loaded according to one embodiment.
Figure 6B:
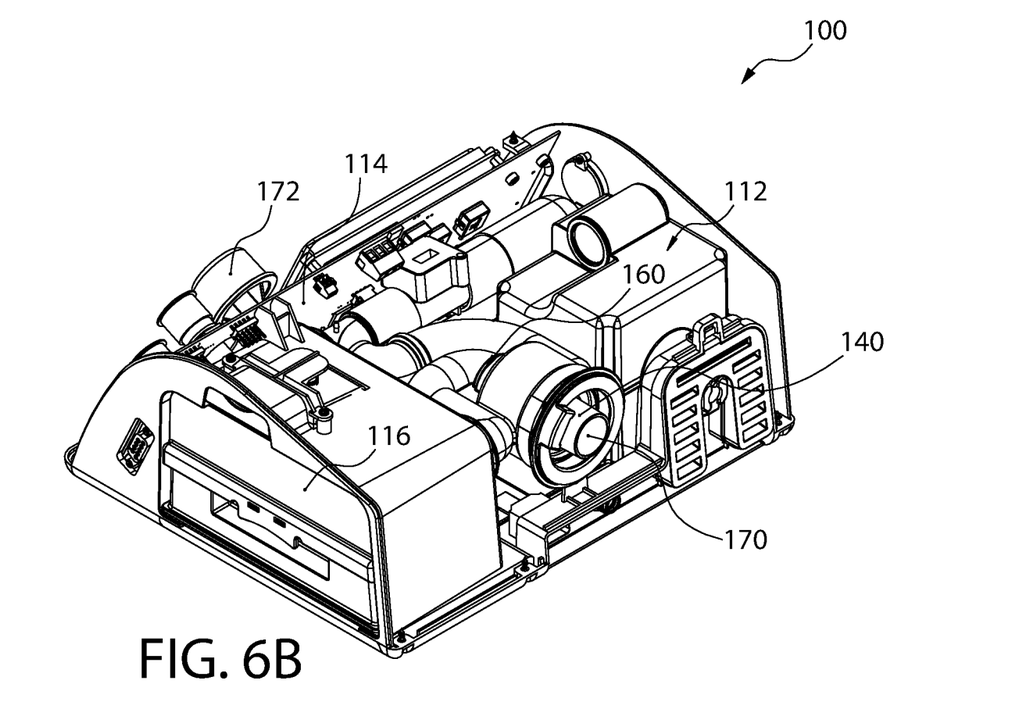
FIG. 6B is a perspective view of assembled components of FIG. 6A, with certain components being transparent.
Figure 7:
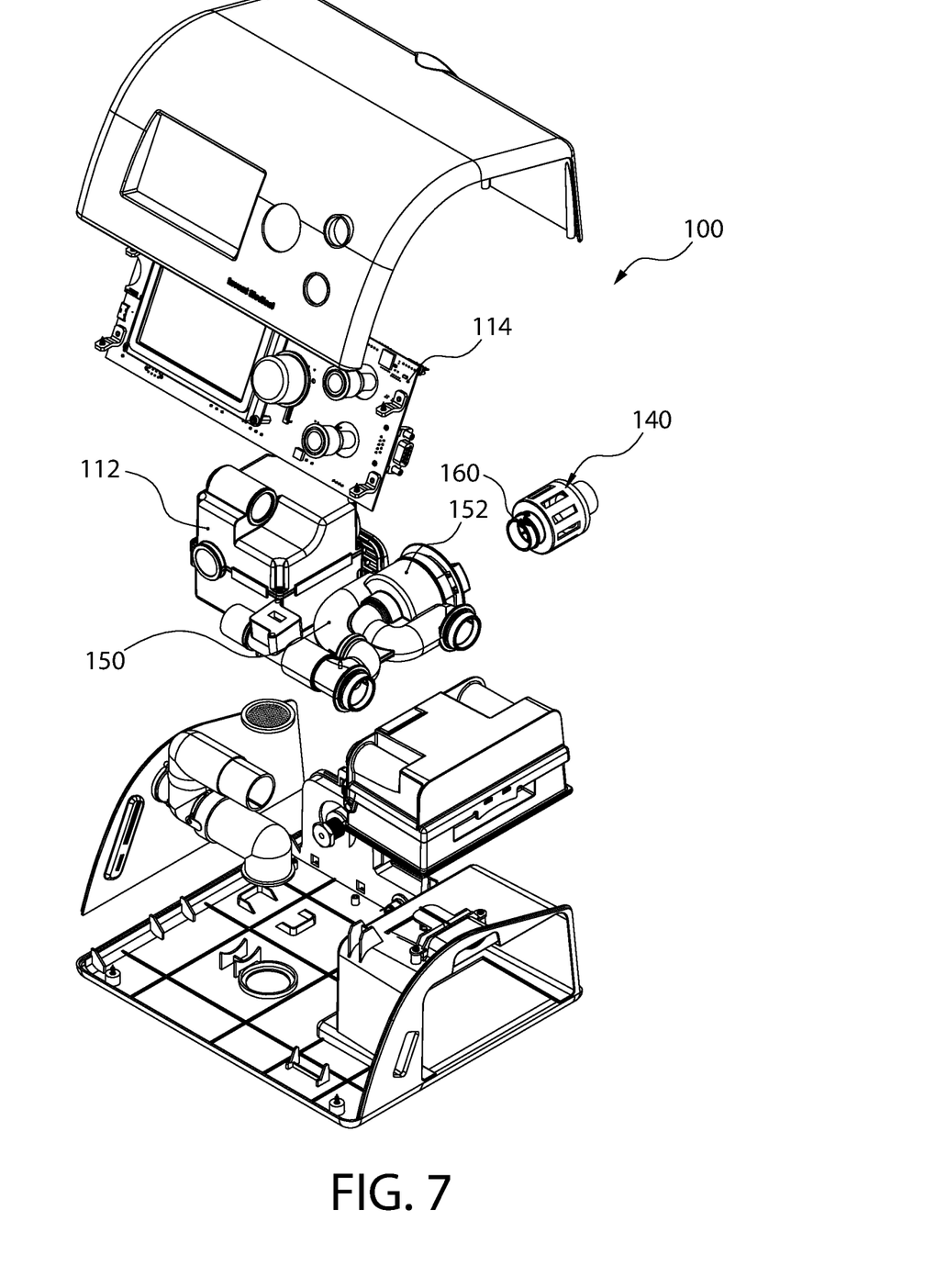
FIG. 7 is an alternate exploded view of a ventilator system according to one embodiment.

With reference now to the views of FIGS. 5-7, a system 100 according to one embodiment has a housing 150 that includes a cavity 152 configured for accepting insertion of the cartridge 140. In certain embodiments, the geometry of the cartridge 140 and the cavity are cubic, so that slidable insertion, removal and seating of the cartridge within the cavity is easily accommodated. In certain embodiments, the geometry of the cartridge 140 is a screw or quick connect mechanism, or another mechanism as known in the art. As will be appreciated by those having ordinary skill in the art, the geometry of the cartridge and the cavity can be any geometry that will allow for insertion, removal and seating of the cartridge within the cavity for proper alignment of gas lines. A locking mechanism 160, such as a hinged cover can also be utilized to secure the cartridge 140 within the cavity 152. Other securing mechanisms known in the art such as snap-fit securement can be utilized. In certain embodiments, the system is configured to ensure that the cartridge is properly inserted, so that the bacteria filter 142 is properly in-line with the check valve 143. This can be accomplished, for example, by a cartridge 140 and cavity 152 geometry that only allows for one-way insertion. Alternatively, a metal contact pair can include one metal contact positioned on the cartridge 140, and a second metal contact positioned within the cavity 152, so that they only touch when the cartridge 140 is properly inserted within the cavity 152. Paired contacts of other materials such as plastic can be used, as would be understood by those having ordinary skill in the art. In certain embodiments, the system will not start, or will signal an error, when improper cartridge insertion is detected.

Rigid component housings can at least partially define the gas flow circuit 120 (as shown with particular reference to FIG. 5). As should already be apparent, the housing structure can be a manifold-type structure for assembly, or alternately can be molded or formed into a single structure. The gas flow circuit can also include flexible conduits, such as plastic tubing, for connecting components of the gas circuit. Openings of the gas flow circuit 120 are configured to interface with openings 121 of the cartridge 140 upon insertion of the cartridge 140 into the cavity 152, so that gas can flow through the bacteria filter and check valve, which are housed within the cartridge 140. Ports are available for connecting the system to air supplies and patient tubing. According to one embodiment, a port 170 is provided on the cartridge for connection (e.g. 118') to patient interface tubing. A knob 172 is included as part of an encoder for user interface settings. One or more protrusions can also be included for interface with a securement mechanism, such as for securement to a medical cart.

In one embodiment, a cartridge for a flow generation system or apparatus includes an inhalation circuit having a first check valve and an exhalation circuit having a bacterial filter. The inhalation circuit and the exhalation circuit merge at a junction downstream of the first check valve and the bacterial filter. The cartridge can be packaged and pre-loaded within the flow generation system, packaged separately, or packaged in bulk as single-use disposable cartridges. Cartridges can be autoclavable for multi-use between different patients, or as mentioned above, can be single-use disposable cartridges. In one embodiment, the inhalation circuit is connected to a first opening in a housing of the cartridge. In one embodiment, the exhalation circuit is connected to a second opening in a housing of the cartridge. In one embodiment, the junction is connected to a third opening in a housing of the cartridge.

By isolating patient exhaled unfiltered air that is potentially contaminated from the main body of the ventilator, cross-contamination between patients can be prevented, even in the case of not using bacteria filters at the ventilator outlet. The bacterial filter and gas circuit configuration only allows filtered air to go back towards dedicated components such as the air pump, and keeps unfiltered or potentially contaminated air forward or downstream of these components. This cross-contamination prevention mechanism can be implemented in the form of a cartridge and it can take several different configurations. In addition to the cartridge, employing an exhalation valve downstream of the main components such as the airflow generator could enhance the ventilator function particularly during exhalation by venting exhaled air to the room. However, it should be noted that this cross-contamination prevention mechanism should work without the exhalation valve. Cartridges according to embodiments of the invention can be disposable or autoclavable.

Figure 8:
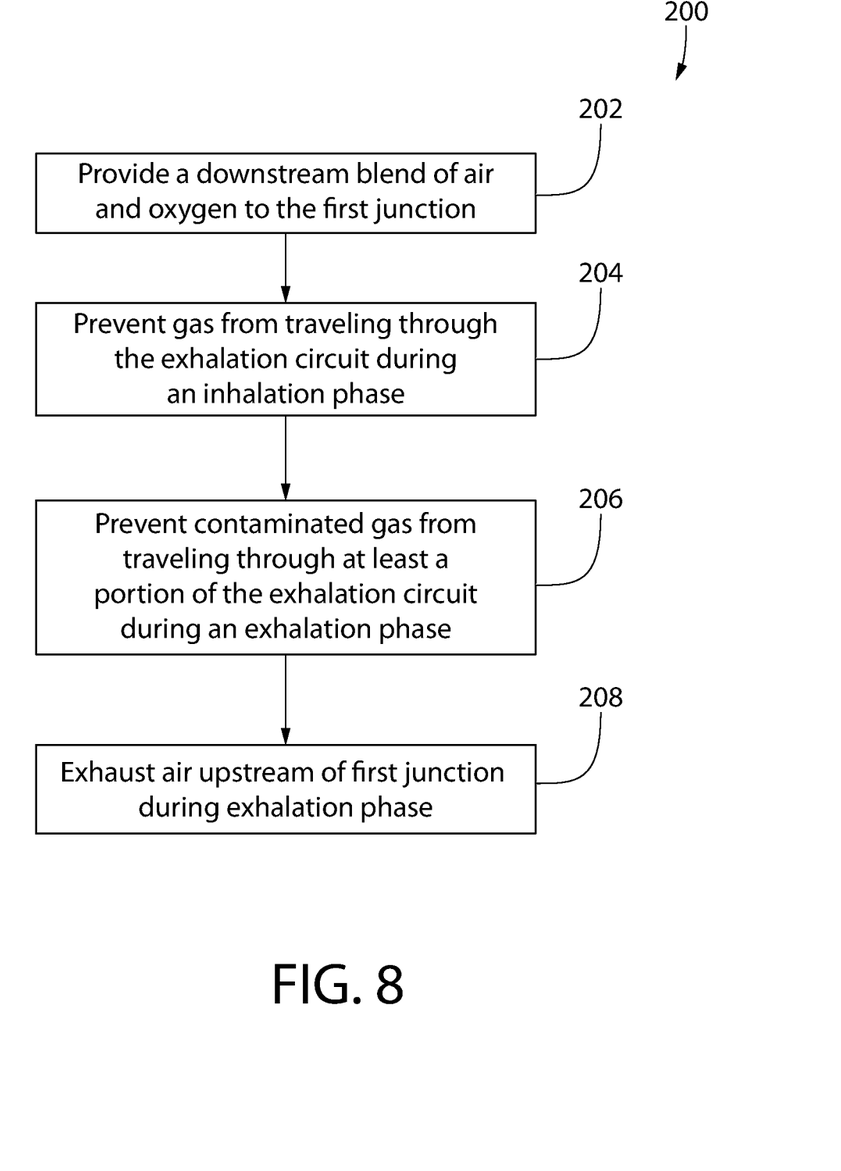
FIG. 8 is a flow chart of a method for providing airflow through a single-limb ventilator system according to one embodiment.

In one embodiment, as shown in FIG. 8, a method 200 for providing gaseous flow through a single-limb ventilator is shown. A downstream gaseous flow is provided to a first junction 202. The first junction has a first branch including an inhalation circuit and a second branch including an exhalation circuit. The inhalation circuit includes a humidifier in-line with a first check valve. The exhalation circuit has a second check valve in-line with a bacterial filter. The inhalation circuit and the exhalation circuit extend to and merge downstream of the first junction at the second junction. Gas is prevented from traveling through at least a portion of the exhalation circuit during an inhalation phase 204, and unfiltered and potentially contaminated gas is prevented from traveling upstream through at least a portion of the exhalation circuit during an exhalation phase 206. This is because unfiltered and potentially contaminated air is prevented from passing through the first check valve or the bacterial filter. Filtered and uncontaminated air can however pass through the bacterial filter. An upstream gaseous flow of air is exhausted upstream of the first junction during an exhalation phase 208. In one embodiment, a portion of the exhalation circuit, the bacterial filter, a portion of the inhalation circuit, and the first check valve are all housed in a removable cartridge. In one embodiment, the second junction is connected to a patient interface. Throughout the embodiments described herein, PI 118 can be or include a mask. In certain embodiments, the mask 118 can be a disposable component and can have for example 6 feet or less, 2 meters, 3 meters or more of disposable tubing that connects to the ventilator. The internal diameter can be for example 10 mm or less, 15 mm, 19 mm, 22 mm or more. These disposable components can also be autoclaved and reused in certain embodiments. The mask and its tubing can be changed out every time between patients and/or treatments. In one embodiment, at least one of the first and second check valves is a pressure actuated check valve. In one embodiment, the exhalation phase is detected by one of a flow sensor and a pressure sensor upstream of the first junction. In one embodiment, the gaseous flow includes a blend of oxygen and ambient air.

Figure 9:
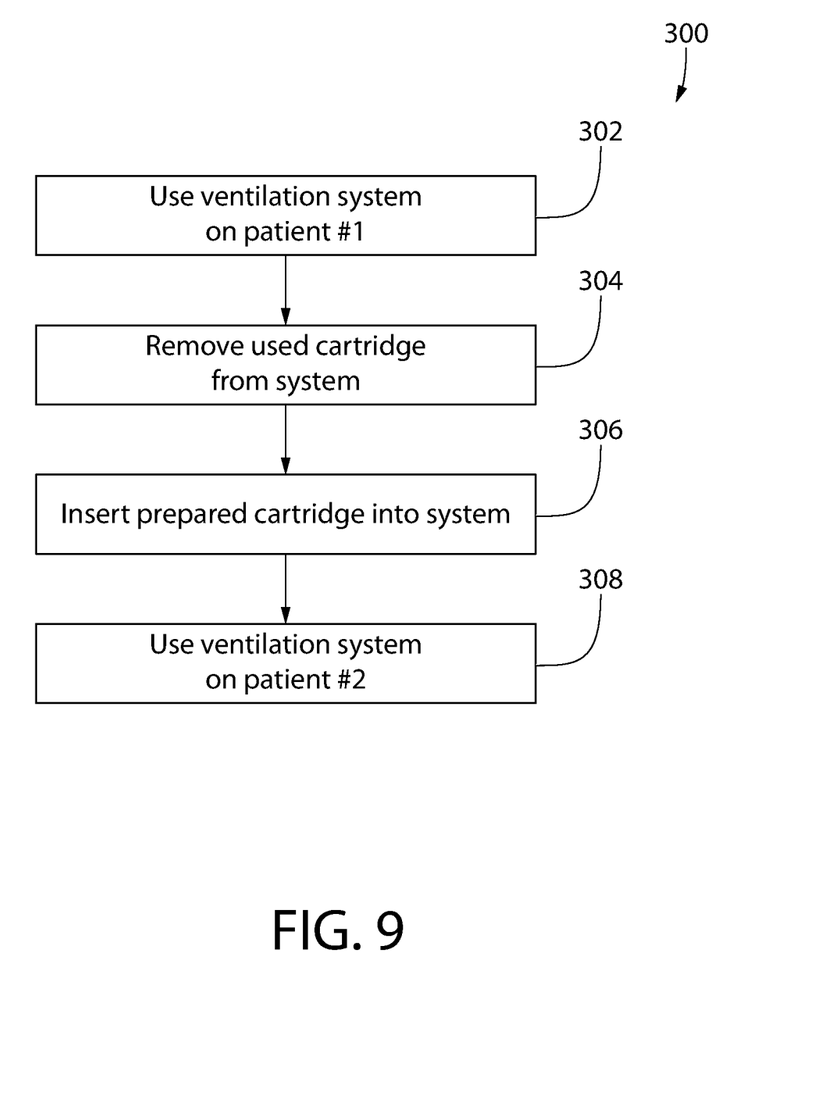
FIG. 9 is a flow chart of a method for preventing cross-contamination in single-limb ventilator systems according to one embodiment.

In one embodiment, as shown in FIG. 9, a method 300 for preventing cross-contamination in single-limb ventilators is described. First, the system is used on a first patient 302, rendering the cartridge used or non-sterile. Then the used cartridge is removed from a cavity in a ventilator system 304. Similar to embodiments described above, the cartridge includes a bacterial filter, and the system includes an airflow generator connected in-line to a humidifier, a first check valve and a patient interface by a gas flow circuit. A housing has the cavity for accepting insertion of the cartridge. When the cartridge is fully inserted into the cavity, the cartridge is connected to the gas flow circuit between a first point downstream of the humidifier and a second point upstream of the humidifier. The removed used cartridge is then replaced with a prepared cartridge 306, which in certain embodiments can be a new cartridge removed from original packaging, or a previously used cartridge that has been cleaned, treated, sterilized or disinfected. In one embodiment, the used cartridge is autoclaved in a machine such as an autoclaving chamber. Once it is autoclaved, the sterile cartridge is considered prepared and inserted back into the cavity of the ventilator system. In one embodiment, the used cartridge is disposed of and replaced with a prepared cartridge that is a new cartridge. With the prepared cartridge inserted into the system, the ventilator system is ready for use by a second patient 308, and the risk of cross-contamination is minimized. In one embodiment, at least one of a flow and a pressure is measured within the gas flow circuit downstream of the airflow generator and upstream of the humidifier, and an exhalation valve is opened based on the measuring. In one embodiment, upstream movement of gas is restricted at a point between the patient interface and the humidifier. In one embodiment, downstream movement of gas is restricted at a point between the bacterial filter and the patient interface. In one embodiment, the used cartridge is twisting, unlatching or slidably removable. In one embodiment, the autoclaved cartridge is twisting, latching or slidably insertable. The cartridge can be secured by a screw, quick connect or other type of connection known in the art. In one embodiment, the cartridge is locked within the cavity. In one embodiment, openings of the gas flow circuit interface with openings of the cartridge upon insertion.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A ventilator system comprising:
   an airflow generator connected in-line to a humidifier, which is connected in line to a first check valve, which is connected in line to a patient interface connection by an inhalation flow circuit;
   a controller electrically coupled to the airflow generator;
   a second check valve connected in-line to a bacterial filter along an exhalation flow circuit, the exhalation flow circuit connected to the inhalation flow circuit between a first junction upstream of the humidifier and a second junction downstream of the first check valve, so as to prevent cross-contamination between the inhalation flow circuit and the exhalation flow circuit;
   an exhalation valve electrically coupled to the controller and connected to the inhalation flow circuit downstream of the airflow generator and upstream of the humidifier;
   a removable cartridge containing the bacterial filter and the first check valve; and
   a housing comprising a cavity, the housing configured so that the first check valve is connected in-line with the inhalation flow circuit and the bacterial filter is connected in-line with the exhalation flow circuit when the cartridge is fully inserted into the cavity.

2. The ventilator system of claim 1, wherein the removable cartridge houses the second junction.

3. The ventilator system of claim 1, wherein the exhalation valve is one of a voice coil actuator, stepper motor valve, proportional solenoid valve and pneumatically piloted balloon valve.

4. The ventilator system of claim 1, wherein the first check valve is configured to restrict an upstream flow of gas.

5. The ventilator system of claim 1, wherein the second check valve is configured to restrict a downstream flow of gas.

6. The ventilator system of claim 1, further comprising a flow sensor electrically coupled to the controller and connected to the inhalation flow circuit downstream of the airflow generator and upstream of the humidifier.

7. The ventilator system of claim 1, further comprising a pressure sensor electrically coupled to the controller and connected to the inhalation flow circuit downstream of the airflow generator and upstream of the humidifier.

8. The ventilator system of claim 1, wherein a first side of the housing is connected to the airflow generator and a second, opposite side of the housing is connected to the humidifier.

9. The ventilator system of claim 1, wherein the housing and at least one of the airflow generator and the humidifier are further contained in a single device housing.

10. A gas flow system comprising:
    an airflow generator connected in-line to a humidifier, a first check valve and a patient interface connection by an inhalation flow circuit;
    a controller electrically coupled to the airflow generator;
    a second check valve connected in-line to a bacterial filter along an exhalation flow circuit, the exhalation flow circuit connected to the inhalation flow circuit between a first junction upstream of the humidifier and a second junction downstream of the first check valve, so as to prevent cross-contamination between the inhalation flow circuit and the exhalation flow circuit;
    a removable cartridge containing the bacterial filter and the first check valve; and
    a housing comprising a cavity, the housing configured so that the first check valve is connected in-line with the inhalation flow circuit and the bacterial filter is connected in-line with the exhalation flow circuit when the cartridge is fully inserted into the cavity.

11. The gas flow system of claim 10, wherein the removable cartridge houses the second junction.

12. The gas flow system of claim 10, further comprising an exhalation valve, wherein the exhalation valve is one of a voice coil actuator, stepper motor valve, proportional solenoid valve and pneumatically piloted balloon valve.

13. The gas flow system of claim 10, wherein the first check valve is configured to restrict an upstream flow of gas.

14. The gas flow system of claim 10, wherein the second check valve is configured to restrict a downstream flow of gas.

15. The gas flow system of claim 10, further comprising a flow sensor electrically coupled to the controller and connected to the inhalation flow circuit downstream of the airflow generator and upstream of the humidifier.

16. The gas flow of claim 10, further comprising a pressure sensor electrically coupled to the controller and connected to the inhalation flow circuit downstream of the airflow generator and upstream of the humidifier.

17. The gas flow system of claim 10, wherein the gas flow system is a ventilator system.

18. The gas flow system of claim 10, wherein a first side of the housing is connected to the airflow generator and a second, opposite side of the housing is connected to the humidifier.

19. The gas flow system of claim 10, wherein the housing, and at least one of the airflow generator and humidifier are further contained in a single device housing.

* * * * *